United States Patent
Beckermann et al.

(10) Patent No.: US 11,395,909 B2
(45) Date of Patent: Jul. 26, 2022

(54) INJECTION PORT DRESSING ASSEMBLY

(71) Applicants: Angela Beckermann, Sauk Centre, MN (US); Lindsay Johnson, Sauk Centre, MN (US)

(72) Inventors: Angela Beckermann, Sauk Centre, MN (US); Lindsay Johnson, Sauk Centre, MN (US)

(*) Notice: Subject to any disclaimer, the term of this patent is extended or adjusted under 35 U.S.C. 154(b) by 76 days.

(21) Appl. No.: 17/003,279

(22) Filed: Aug. 26, 2020

(65) Prior Publication Data

US 2022/0062613 A1    Mar. 3, 2022

(51) Int. Cl.
*A61M 25/02*    (2006.01)
*A61M 39/02*    (2006.01)
*A61F 13/00*    (2006.01)

(52) U.S. Cl.
CPC ......... *A61F 39/0247* (2013.01); *A61F 13/00* (2013.01); *A61M 25/02* (2013.01); *A61F 2013/00412* (2013.01); *A61M 2025/028* (2013.01); *A61M 2025/0273* (2013.01); *A61M 2039/0205* (2013.01); *A61M 2039/0288* (2013.01)

(58) Field of Classification Search
CPC .............. A61M 39/0247; A61M 25/02; A61M 2025/0273; A61M 2025/028; A61M 2039/0205; A61M 2039/0288; A61F 13/00; A61F 2013/00412

See application file for complete search history.

(56) References Cited

U.S. PATENT DOCUMENTS

| | | |
|---|---|---|
| 5,449,349 A | 9/1995 | Sallee |
| 2004/0002670 A1 | 1/2004 | Mothersbaugh |
| 2013/0018322 A1* | 1/2013 | Wright ................. A61F 13/023 604/180 |
| 2013/0102945 A1 | 4/2013 | Long |
| 2013/0102979 A1 | 4/2013 | Coulthard |

FOREIGN PATENT DOCUMENTS

WO    WO2012106051    8/2012

\* cited by examiner

*Primary Examiner* — Deanna K Hall

(57) ABSTRACT

An injection port dressing assembly for covering an injection port in a patient includes a dressing that is positionable around an injection port in a patient to inhibit bacteria from accessing the injection port. The dressing has a tube opening therein to accommodate an injection tube from the injection port. A dome is provided and the dome is coupled to the dressing to cover the injection port when the dressing is placed on the patient. The dome is comprised of a translucent material to facilitate the injection port to be visible through the dome. An adhesive layer is coupled to the dressing to adhesively engage the patient's skin.

6 Claims, 5 Drawing Sheets

INJECTION PORT DRESSING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to dressing devices and more particularly pertains to a new dressing device for covering an injection port in a patient.

(2) Description of Related Art Including Information Disclosed Under 37 CFR 1.97 and 1.98

The prior art relates to dressing devices including an I.V. dressing that includes a triangular housing and a channel extending into the housing. The prior art discloses a wound dressing that has a fluid channel integrated therein for facilitating a wound to be flushed with a fluid. The prior art discloses an injection port dressing that include a dome that is positioned between a pair of adhesive dressings. The prior art discloses an injection port dressing that includes a dome and a channel extending into the dome for accommodating an injection tube of the injection port. The prior art discloses a wound dressing that can be evacuated with vacuum pressure for reducing pressure on a wound.

BRIEF SUMMARY OF THE INVENTION

An embodiment of the disclosure meets the needs presented above by generally comprising a dressing that is positionable around an injection port in a patient to inhibit bacteria from accessing the injection port. The dressing has a tube opening therein to accommodate an injection tube from the injection port. A dome is provided and the dome is coupled to the dressing to cover the injection port when the dressing is placed on the patient. The dome is comprised of a translucent material to facilitate the injection port to be visible through the dome. An adhesive layer is coupled to the dressing to adhesively engage the patient's skin.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
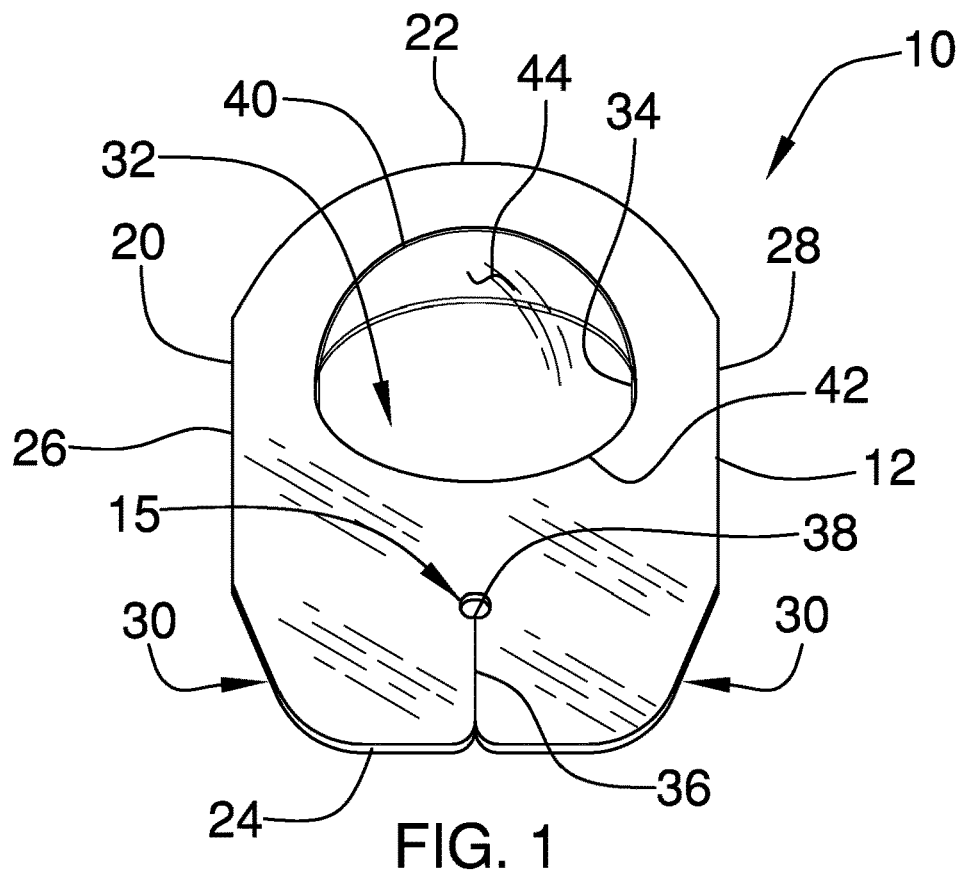
FIG. 1 is a top perspective view of an injection port dressing assembly according to an embodiment of the disclosure.
Figure 2:
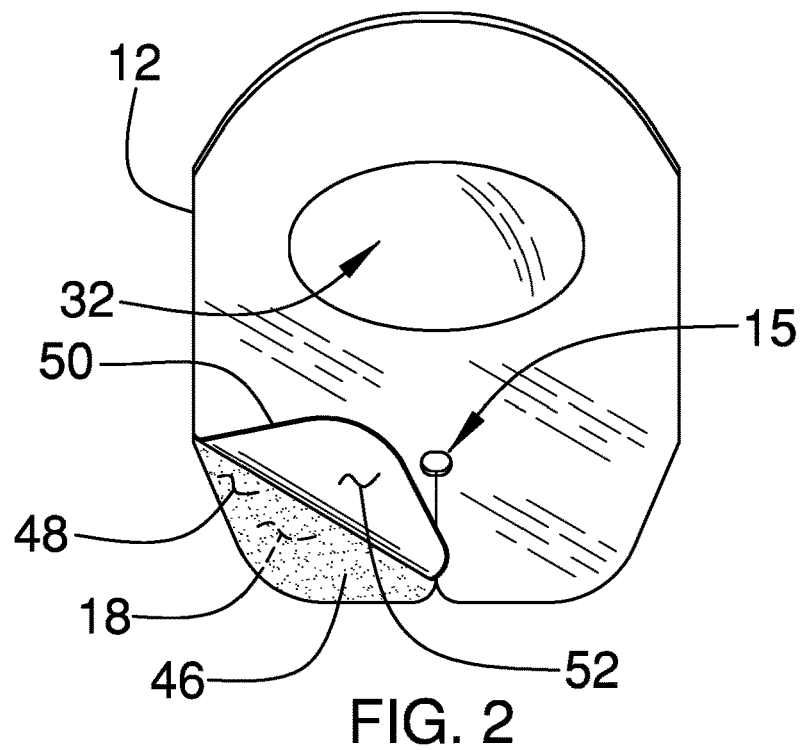
FIG. 2 is a bottom perspective view of an embodiment of the disclosure.
Figure 3:
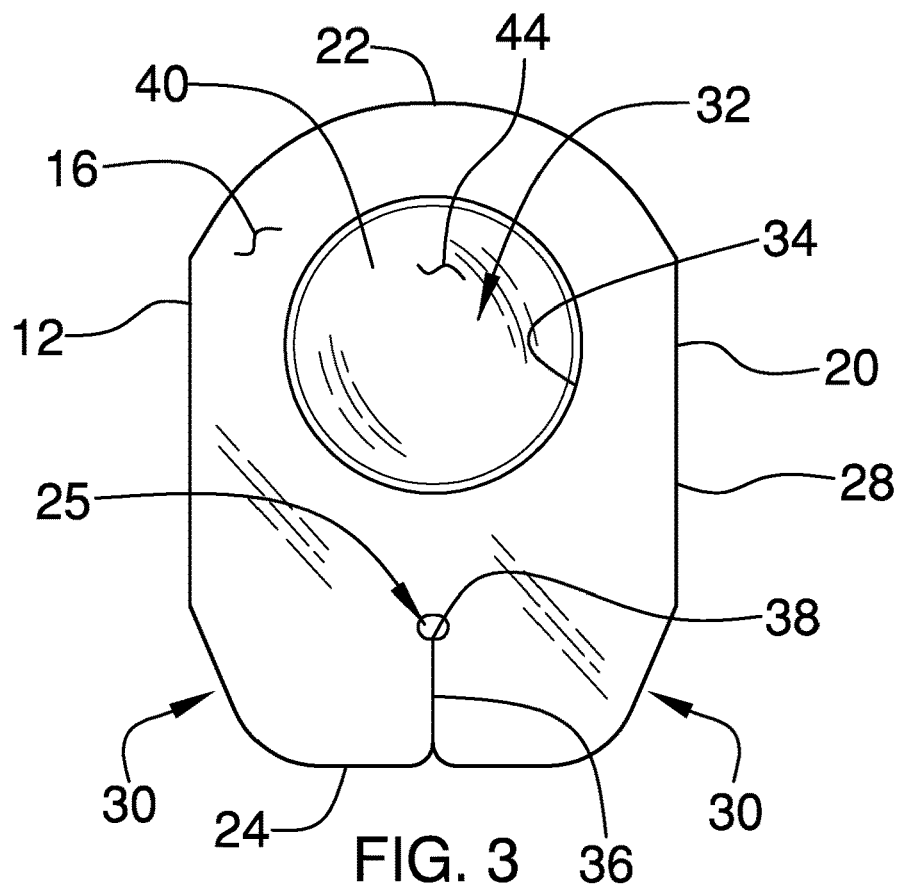
FIG. 3 is a top view of an embodiment of the disclosure.
Figure 4:
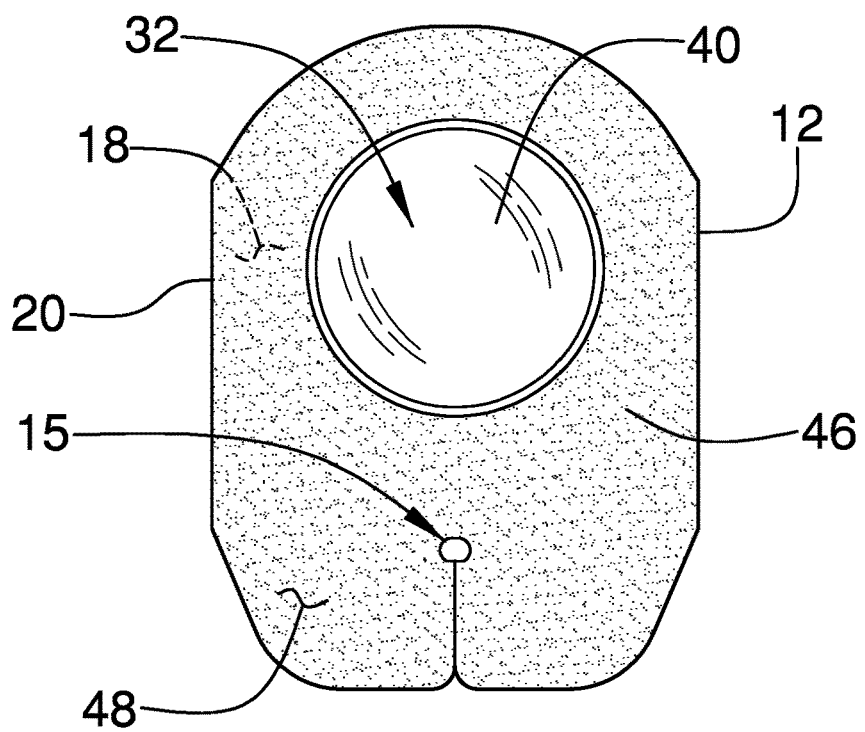
FIG. 4 is a bottom view of an embodiment of the disclosure.
Figure 5:
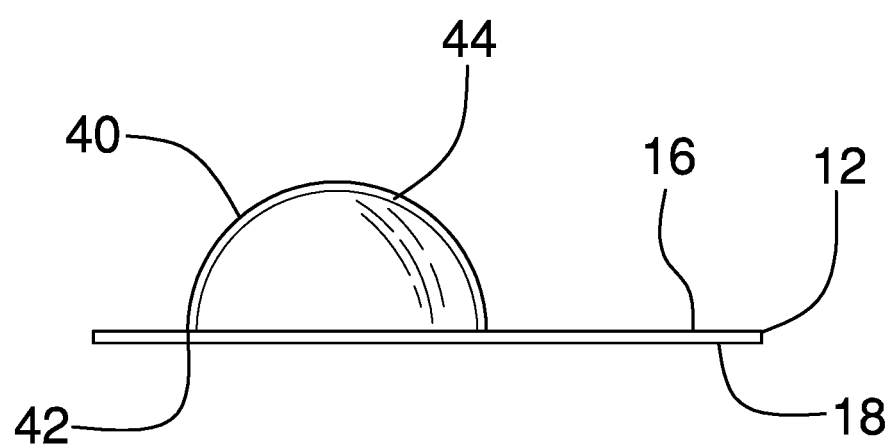
FIG. 5 is a right side view of an embodiment of the disclosure.
Figure 6:
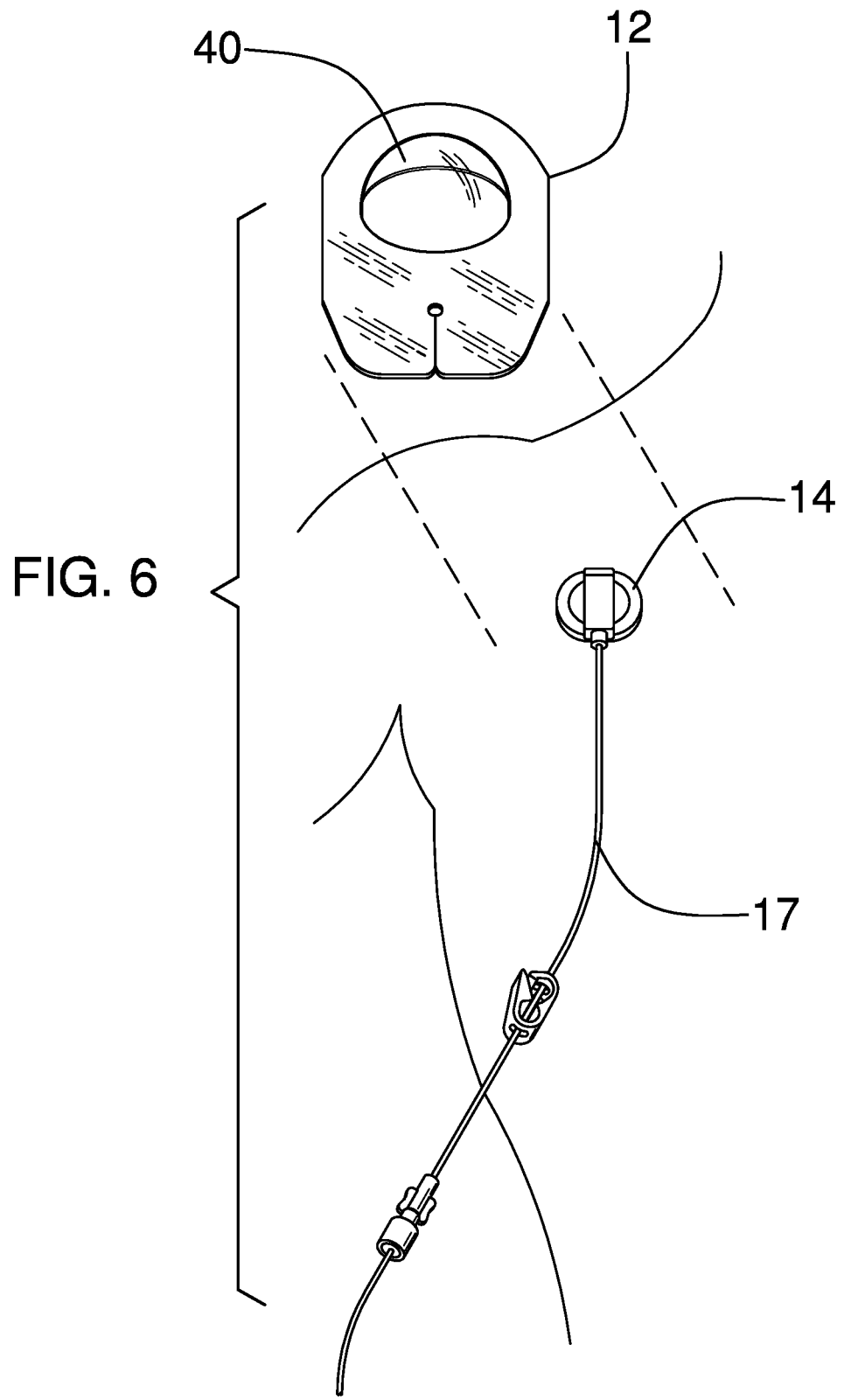
FIG. 6 is a perspective in-use view of an embodiment of the disclosure showing a dressing being positioned over an injection port.
Figure 7:
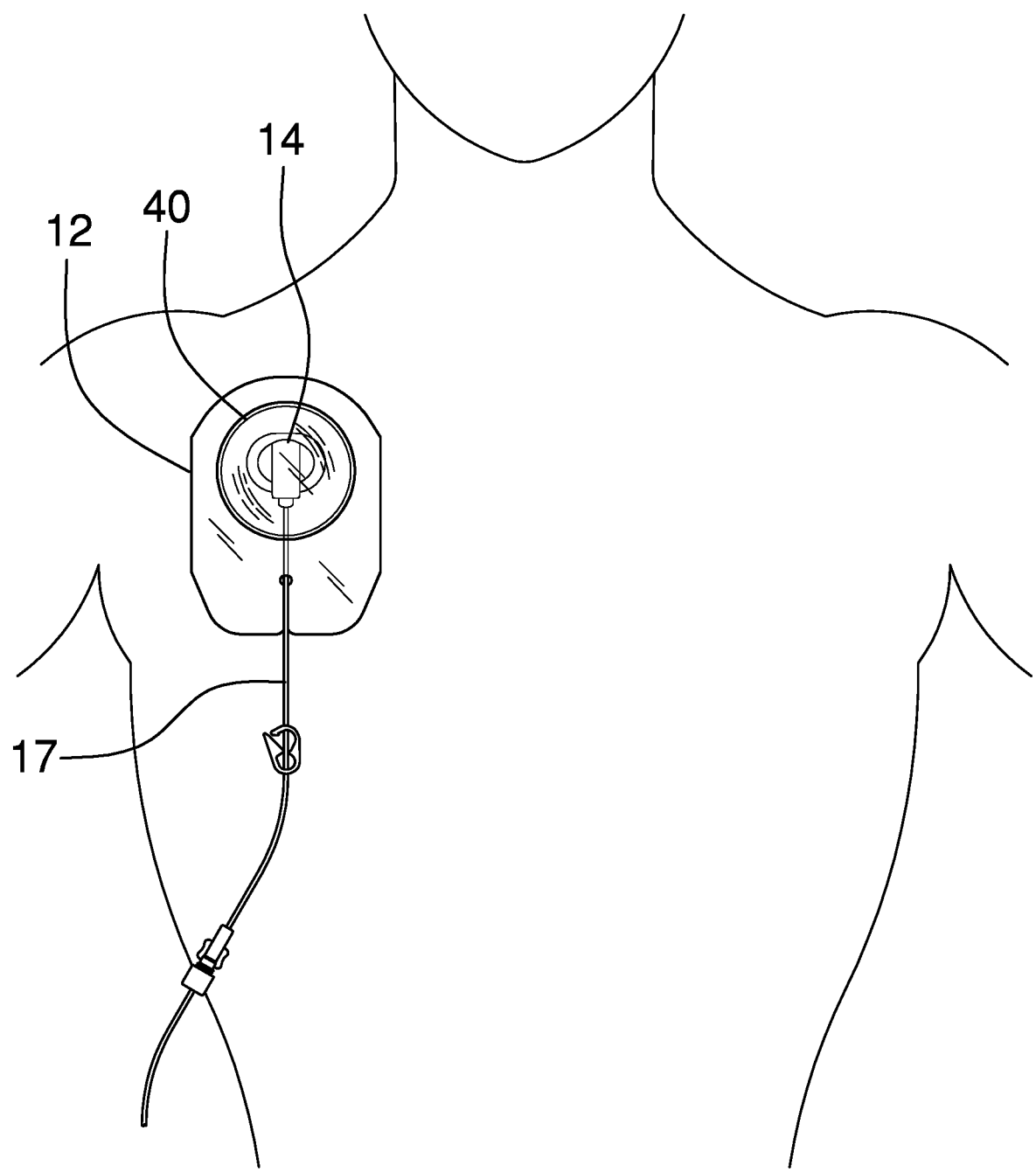
FIG. 7 is a perspective in-use view of an embodiment of the disclosure showing a dressing in place over an injection port.

With reference now to the drawings, and in particular to FIGS. 1 through 7 thereof, a new dressing device embodying the principles and concepts of an embodiment of the disclosure and generally designated by the reference numeral 10 will be described.

As best illustrated in FIGS. 1 through 7, the injection port dressing assembly 10 generally comprises a dressing 12 that is positionable around an injection port 14 in a patient to inhibit bacteria from accessing the injection port 14. The injection port 14 may be a surgically installed Huber needle port commonly employed in an in-patient medical setting. The dressing 12 has a tube opening 15 therein to accommodate an injection tube 17 from the injection port 14. Additionally, the dressing 12 may be comprised of a gauze-like material common to medical dressings.

The dressing 12 has a top surface 16, a bottom surface 18 and a perimeter edge 20 extending therebetween, and the perimeter edge 20 has a back side 22, a front side 24, a first lateral side 26 and a second lateral side 28. The back side 22 is rounded outwardly between the first lateral side 26 and the second lateral side 28. Each of the first lateral side 26 and the second lateral side 28 has an angled portion 30 which angles inwardly at an intersection between the first lateral side 26, the second lateral side 28 and the front side 24.

The dressing 12 has a hole 32 extending through the top surface 16 and the bottom surface 18. In this way the hole 32 surrounds the injection port 14 when the dressing 12 is applied to the patient. The hole 32 is positioned adjacent to a center of the dressing 12 and the hole 32 has a bounding edge 34. The dressing 12 has a cut 36 extending from the front side 24 toward the hole 32 and the cut 36 has a terminal end 38. The tube opening 15 extends through the top surface 16 and the bottom surface 18. Moreover, the tube opening 15 is aligned with the terminal end 38 to facilitate the dressing 12 to be positioned around the injection tube 17 for positioning the injection tube 17 in the tube opening 15. The cut 36 and the tube opening 15 are each centrally positioned between the first lateral side 26 and the second lateral side 28 of the perimeter edge 20.

A dome 40 is coupled to the dressing 12 to cover the injection port 14 when the dressing 12 is placed on the patient. The dome 40 is comprised of a translucent material to facilitate the injection port 14 to be visible through the dome 40. In this way the injection port 14 can be visualized and assessed by a medical provider without the need to remove the dressing 12. Existing injection port dressings are stretched over the injection port 14, which results in uncomfortable tugging of the patient's skin. Additionally, the outer edges of existing injection port dressings tend to roll up from the tension that results from being stretched over the injection port 14. The dome 40 facilitates the dressing 12 to lie completely flat on the user's skin while the dome 40 covers the injection port 14. In this way the dome 40 alleviates the problems of tugging and rolling of the edges of conventional dressings.

The dome 40 has a bottom edge 42 and an outer surface 44, the outer surface 44 is concavely arcuate with respect to the bottom edge 42, and the bottom edge 42 is bonded to the top surface 16 of the dressing 12. Moreover, the bottom edge 42 is aligned with and is coextensive with the bounding edge 34 of the hole 32 in the dressing 12 such that the dome 40 covers the hole 32. The outer surface 44 curves upwardly with respect to the top surface 16 of the dressing 12. Additionally, the dome 40 may be comprised of a non-latex, medically approved material.

An adhesive layer 46 is coupled to the dressing 12 to adhesively engage the patient's skin. The adhesive layer 46 is bonded to the bottom surface 18 of the dressing 12 and the adhesive layer 46 has an exposed surface 48 with respect to the dressing 12. The adhesive layer 46 may comprise a non-toxic skin adhesive that is approved for use in a surgical environment. A protective sheet 50 is provided that has a first surface 52 and the first surface 52 removably engages the exposed surface 48 of the adhesive layer 46. The first surface 52 completely covers the exposed surface 48 for protecting the adhesive layer 46 until the dressing 12 is applied to the patient.

In use, the protective sheet 50 is removed from the adhesive layer 46 and the dome 40 is placed over the injection port 14. The injection tube 17 is extended through the tube opening 15 and the dressing 12 is then flattened out on the patient's skin for retaining the dome 40 over the injection port 14 and to protect the injection port 14 from exposure to bacteria. The dome 40 facilitates the injection port 14 to be covered and to be visible while the dressing 12 protects the injection port 14 from infection. Additionally, the dressing 12 does not uncomfortably tug on the patient's skin in the manner of existing injection port dressings to enhance comfort for the patient. The dressing 12 is removed when an injection is to be administered into the injection port 14.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. An injection port dressing assembly for covering an injection port on a patient, said assembly comprising:

a dressing is positionable around an injection port in a patient wherein said dressing is configured to inhibit bacteria from accessing the injection port, said dressing having a tube opening therein wherein said tube opening is configured to accommodate an injection tube from the injection port, wherein said dressing has a top surface, a bottom surface and a perimeter edge extending therebetween, said perimeter edge having a back side, a front side, a first lateral side and a second lateral side, said back side being rounded outwardly between said first lateral side and said second lateral side, said dressing having a hole extending through said top surface and said bottom surface wherein said hole is configured to surround the injection port when said dressing is applied to the patient, said hole being positioned adjacent to a center of said dressing, said hole having a bounding edge, each of said first lateral edge and said second lateral edge having a respective angled portion wherein a portion of said dressing extending between said first lateral side to said second lateral side and from said tube opening to said front side is trapezoidal;

a cut extending from said front side toward said hole, said cut having a terminal end, said cut having a straight section and a flared portion, said flared portion being adjacent to said front side;

a dome being coupled to said dressing wherein said dome is configured to cover the injection port when said dressing is placed on the patient, said dome being comprised of a translucent material wherein said dome is configured to facilitate the injection port to be visible through said dome; and an adhesive layer being coupled to said dressing wherein said adhesive layer is configured to adhesively engage the patient's skin.

2. The assembly according to claim 1, wherein said tube opening extends through said top surface and said bottom surface, said tube opening being aligned with said terminal end wherein said cut is configured to facilitate said dressing to be positioned around the injection tube to facilitate the injection tube to be positioned in said tube opening.

3. The assembly according to claim 1, wherein said dome has a bottom edge and an outer surface, said outer surface being concavely arcuate with respect to said bottom edge, said bottom edge being bonded to said top surface of said dressing.

4. The assembly according to claim 3, wherein said bottom edge is aligned with and being coextensive with said bounding edge of said hole in said dressing such that said dome covers said hole, said outer surface curving upwardly with respect to said top surface of said dressing.

5. The assembly according to claim 1, wherein:
said adhesive layer is bonded to said bottom surface of said dressing, said adhesive layer having an exposed surface with respect to said dressing; and
said assembly includes a protective sheet having a first surface, said first surface removably engaging exposed surface of said adhesive layer for protecting said adhesive layer, said first surface completely covering said exposed surface.

6. An injection port dressing assembly for covering an injection port on a patient, said assembly comprising:
a dressing being positionable around an injection port in a patient wherein said dressing is configured to inhibit bacteria from accessing the injection port, said dressing having a tube opening therein wherein said tube opening is configured to accommodate an injection tube from the injection port, said dressing having a top surface, a bottom surface and a perimeter edge extending therebetween, said perimeter edge having a back side, a front side, a first lateral side and a second lateral side, said back side being rounded outwardly between said first lateral side and said second lateral side, said dressing having a hole extending through said top surface and said bottom surface wherein said hole is configured to surround the injection port when said dressing is applied to the patient, said hole being positioned adjacent to a center of said dressing, said hole having a bounding edge, each of said first lateral edge and said second lateral edge having a respective angled portion wherein a portion of said dressing extending between said first lateral side to said second lateral side and from said tube opening to said front side is trapezoidal, said dressing having a cut extending from said front side toward said hole, said cut having a terminal end, said cut having a straight section and a flared portion, said flared portion being adjacent to said front side, said tube opening extending through said top surface and said bottom surface, said tube opening being aligned with said terminal end wherein said cut is configured to facilitate said dressing to be positioned around the injection tube to facilitate the injection tube to be positioned in said tube opening;
a dome being coupled to said dressing wherein said dome is configured to cover the injection port when said dressing is placed on the patient, said dome being comprised of a translucent material wherein said dome is configured to facilitate the injection port to be visible through said dome, said dome having a bottom edge and an outer surface, said outer surface being concavely arcuate with respect to said bottom edge, said bottom edge being bonded to said top surface of said dressing, said bottom edge being aligned with and being coextensive with said bounding edge of said hole in said dressing such that said dome covers said hole, said outer surface curving upwardly with respect to said top surface of said dressing;
an adhesive layer being coupled to said dressing wherein said adhesive layer is configured to adhesively engage the patient's skin, said adhesive layer being bonded to said bottom surface of said dressing, said adhesive layer having an exposed surface with respect to said dressing; and
a protective sheet having a first surface, said first surface removably engaging exposed surface of said adhesive layer for protecting said adhesive layer, said first surface completely covering said exposed surface.

\* \* \* \* \*